United States Patent
Tanahashi

(10) Patent No.: US 8,082,103 B2
(45) Date of Patent: Dec. 20, 2011

(54) $CO_2$ CONCENTRATION CORRECTING APPARATUS AND $CO_2$ CONCENTRATION CORRECTING METHOD

(75) Inventor: Shuichi Tanahashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 12/805,177

(22) Filed: Jul. 15, 2010

(65) Prior Publication Data

US 2010/0286914 A1    Nov. 11, 2010

Related U.S. Application Data

(63) Continuation of application No. PCT/JP2008/050546, filed on Jan. 17, 2008.

(51) Int. Cl.
*G06F 19/00*    (2011.01)

(52) U.S. Cl. .......... 702/2; 702/8; 702/199; 250/253; 250/264; 250/267; 250/302; 356/307; 23/295 S; 385/900

(58) Field of Classification Search .......... 702/2, 8, 702/199; 250/253, 264, 267, 302; 356/307; 23/295 S; 385/900
See application file for complete search history.

(56) References Cited

U.S. PATENT DOCUMENTS

| | | | |
|---|---|---|---|
| 6,397,162 B1 * | 5/2002 | Ton | 702/136 |
| 2009/0227161 A1 * | 9/2009 | Lambert | 441/29 |

FOREIGN PATENT DOCUMENTS

JP    2004-305069    11/2004

OTHER PUBLICATIONS

Gen Inoue, "Taiki kara Mita Nisanka Tanso Shushi (Balance in Carbon Dioxide from a Standpoint of Atmosphere)," Global Environmental Research, Dec. 8, 2004, vol. 9, No. 2, 14 pages.
A. Angert et al., "Drier summers cancel out the $CO_2$ uptake enhancement induced by warmer springs," Proceedings of the National Academy of Sciences of the United States of America, Aug. 2, 2005, vol. 102, No. 31, 6 pages.
Extended European Search Report for corresponding European Patent Application No. 08703401.3, issued on May 30, 2011.
D. Crisp et al., "The Orbiting Carbon Observatory (OCO) Mission," Advances in Space Research, vol. 34, No. 4, 2004, pp. 700-709.
D. S. Schimel et al., "Recent Patterns and Mechanisms of Carbon Exchange by Terrestrial Ecosystems," Nature, vol. 414, No. 6860, Nov. 8, 2001, pp. 169-172.

(Continued)

*Primary Examiner* — Sujoy Kundu
(74) *Attorney, Agent, or Firm* — Staas & Halsey LLP

(57) ABSTRACT

Hourly $CO_2$ concentration, amount of solar radiation, and plant distribution information are calculated through observation from predetermined satellites. A concentration of $CO_2$ absorbed by plant-chlorophyll per each time unit is calculated. By adding up the $CO_2$ concentration on the earth and the concentration of $CO_2$ absorbed by the plant-chlorophyll, a $CO_2$ concentration obtained provided that no plant-chlorophyll exist is calculated for a certain period. Thereafter, a mean concentration of $CO_2$ that is absorbed according to changes in the distribution of plant-chlorophyll is calculated on the basis of a monthly mean solar radiation amount and plant-chlorophyll distribution information. By subtracting the $CO_2$ concentration, which is a mean, from the total $CO_2$ concentration, a $CO_2$ concentration, which is a normal, is calculated.

6 Claims, 7 Drawing Sheets

OTHER PUBLICATIONS

D. S. Schimel, "Terrestrial Ecosystems and the Carbon Cycle," Global Change Biology, vol. 1, No. 1, Feb. 1995, pp. 77-91 and Abstract.

Wilfred M. Post et al., "The Global Carbon Cycle," American Scientist, vol. 78, 1990, pp. 310-326.

Daniel Feldman, "Retrieval of Carbon Dioxide Concentration from AIRS Thermal Emission Data," California Institute of Technology, Nov. 25, 2003, pp. 1-11.

Thomas R. Livermore et al., "The NASA Orbiting Carbon Observatory Mission," Aerospace Conference, 2008 IEEE, IEEE, Piscataway, NJ, Mar. 1, 2008, pp. 1-6.

International Search Report for PCT/JP2008/050546, mailed on Mar. 25, 2008.

* cited by examiner

US 8,082,103 B2

$CO_2$ CONCENTRATION CORRECTING APPARATUS AND $CO_2$ CONCENTRATION CORRECTING METHOD

CROSS-REFERENCE TO RELATED APPLICATION(S)

This application is a continuation of International Application No. PCT/JP2008/050546, filed on Jan. 17, 2008, the entire contents of which are incorporated herein by reference.

FIELD

The embodiment discussed herein is directed to a $CO_2$ concentration correcting apparatus and a $CO_2$ concentration correcting method.

BACKGROUND

Global warming with its increase in $CO_2$ levels has become a social issue. Thus, it is necessary to reduce $CO_2$ emissions and reduce excessive emitted $CO_2$ through green campaigns, for example, planting plants. For this reason, objectives have been established to accurately understand the latest distribution of $CO_2$, plants that absorb $CO_2$ by photosynthesis, and the distribution of chlorophyll.

Conventionally, the amount of $CO_2$ is directly observed by instruments with which, for example, aircraft are equipped. However, because the observed values obtained by the instruments through their measurements is information limited to a specific point, the spatial actual amount and the distribution of chlorophyll cannot be uniformly understood. Thus, the amount of $CO_2$ on the earth cannot be accurately known. Therefore, a definite policy of green schemes cannot be established and only limited measurements have been taken for in regions where tree-planting can be carried out.

However, the Greenhouse Gases Observing Satellite (GOSAT) and the US Orbiting Carbon Observatory (OCO), which can observe the $CO_2$ concentration on the earth, have been developed in recent years. Observations by the GOSAT and OCO allow us to know the distribution of $CO_2$. Accordingly, global distribution data on the $CO_2$ concentrations can be obtained.

For example, Patent Document 1 discloses, as conventional technologies related to the concentration distribution of $CO_2$, a planting support system that can carry out appropriate planting schemes in consideration of the chronological changes of plants by calculating the amount of $CO_2$ in the atmosphere in accordance with planting with regard to each type of plant.

Patent Document 1: Japanese Laid-open Patent Publication No. 2000-12345

DISCLOSURE OF INVENTION

Problem to be Solved by the Invention

Conventionally, $CO_2$ concentration is observed by the GOSAT and the observed $CO_2$ concentration is regarded as the $CO_2$ concentration on the earth. However, there is a problem in that the data that is obtained by the GOSAT through observations is not the value of the $CO_2$ concentration for the normal weather. In other words, for the value of the $CO_2$ concentration that is used as a $CO_2$ reduction target value, it is necessary to consider the effects from plants and chlorophyll that absorb $CO_2$ by photosynthesis. However, the current methods do not consider such effects.

In other words, effects from the weather on the $CO_2$ that plants and chlorophyll absorb are not considered for the value of the $CO_2$ concentration observed by these satellites. There is a problem in that, although there are seasonal variations and daily variations in the amount of absorbed $CO_2$ according to the activities of vegetation according to changes in the amount of solar radiation, corrections are not made for those variations and changes. Specifically, for example, when there are a lot of sunny days (a large amount of solar radiation) and plants actively photosynthesize, a smaller amount of $CO_2$ is observed compared to a year with a lot of cloudy days.

SUMMARY

According to an aspect of an embodiment of the invention, an apparatus includes an observed $CO_2$ amount storage unit (14) that stores an observed $CO_2$ amount that is an amount of $CO_2$ that is observed in an observation region; a plant-chlorophyll distribution information storage unit (11) that stores plant-chlorophyll distribution information on distribution of plant-chlorophyll in the observation region; a solar radiation amount storage unit (13) that stores an amount of solar radiation in the observation region; an absorbed $CO_2$ amount calculating unit that calculates an absorbed $CO_2$ amount that is an amount of $CO_2$ that is absorbed by the plant-chlorophyll on the basis of the plant-chlorophyll distribution information and the amount of solar radiation; a total $CO_2$ amount calculating unit that calculates a total $CO_2$ amount by adding up the observed $CO_2$ amount and the absorbed $CO_2$ amount; an average solar radiation amount storage unit that stores an average solar radiation amount in the observation region; an average absorbed $CO_2$ amount calculating unit that calculates an average absorbed $CO_2$ amount that is an average amount of $CO_2$ that is absorbed by plant-chlorophyll when a solar radiation amount is the average solar radiation amount; and a corrected $CO_2$ amount calculating unit that calculates a corrected $CO_2$ amount by subtracting the average absorbed $CO_2$ amount from the total $CO_2$ amount.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

DESCRIPTION OF EMBODIMENT

Figure 1:
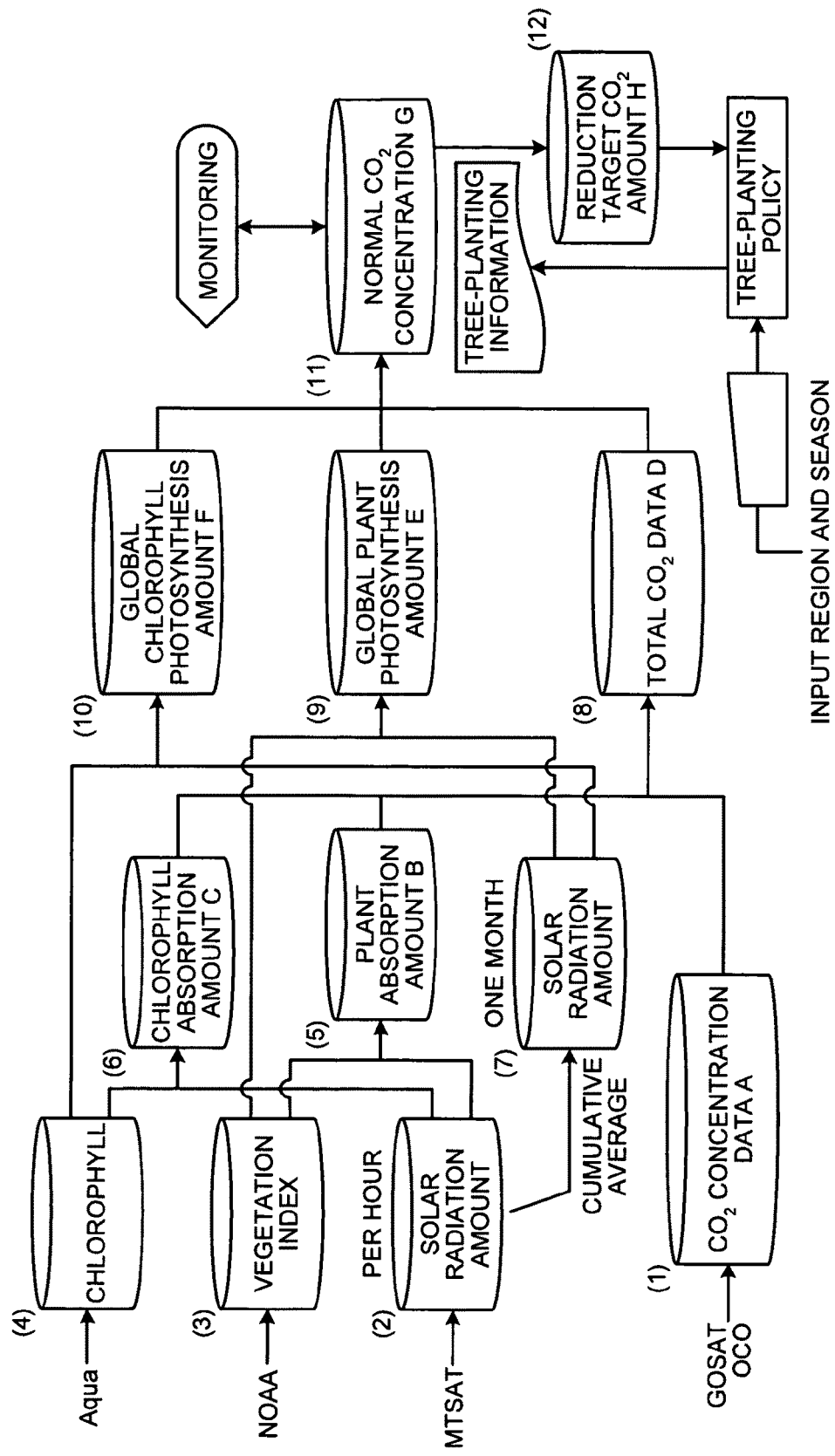
FIG. 1 is an explanatory diagram representing an overview and features of a $CO_2$ concentration correcting apparatus according to a first embodiment.

Embodiments of a $CO_2$ concentration correcting apparatus, a $CO_2$ concentration correcting method, and a $CO_2$ concentration correcting program according to the present invention will be explained below with reference to the accompanying drawings. Explanations of an overview of a plurality of observation satellites that are used in the embodiments, of an overview and features of a $CO_2$ concentration correcting apparatus according to a first embodiment, of an overview of a process of the $CO_2$ concentration correcting apparatus, for a configuration of the $CO_2$ concentration correcting apparatus, and of a flow of the process of the $CO_2$ concentration correcting apparatus will be provided in the sequence they appear in this sentence, and explanations of the effects from the first embodiment will be provided last.

Explanation of Overview of Observation Satellites

A $CO_2$ concentration correcting apparatus 1 illustrated in the first embodiment receives observation information (a $CO_2$ concentration, an amount of solar radiation, a distribution amount of plants, and a distribution amount of chlorophyll) and corrects the $CO_2$ concentration on the basis of the observation information. First, an overview of the observation satellites will be given.

The Greenhouse Gases Observing Satellite (GOSAT) is a greenhouse gas observation technology satellite that is a satellite that observes the $CO_2$ concentration on the earth. The Orbiting Carbon Observatory (OCO) is a US $CO_2$ observation satellite that can observe the $CO_2$ concentration as the GOSAT can.

The NOAA satellite is a satellite that was launched by the National Oceanic and Atmospheric Administration (NOAA). The NOAA satellite can obtain data on vegetation (vegetation index SR) on the earth through observation.

The Multi-functional Transport Satellites (MTSAT) are transportation multi-purpose satellites that observe the amount of solar radiation on the basis of the distribution of clouds over the earth. Besides using MTSAT, the amount of solar radiation can be estimated from data from the Geostationary Operational Environmental Satellites (GOES), which are US stationary weather satellites and the Metrology Satellites (METEOSAT), which are European weather satellites.

Aqua is an US earth observation satellite for observing, from space, various physical quantities (environmental data) relating to the circulation of water and energy and for integrally examining mutual interactions between the atmosphere, the ocean, and continents and effects thereof on changes in the earth system. Aqua is equipped with a MODIS sensor and observes the amount of chlorophyll using the MODIS sensor. Chlorophyll is a plant microorganism. Chlorophyll exists near the ocean surface of the earth and absorbs $CO_2$ by photosynthesis. The absorbance of $CO_2$ by chlorophyll influences the water temperature of the ocean surface and the amount of salt on the ocean surface.

Overview and Features of $CO_2$ Concentration Correcting Apparatus

Figure 2:
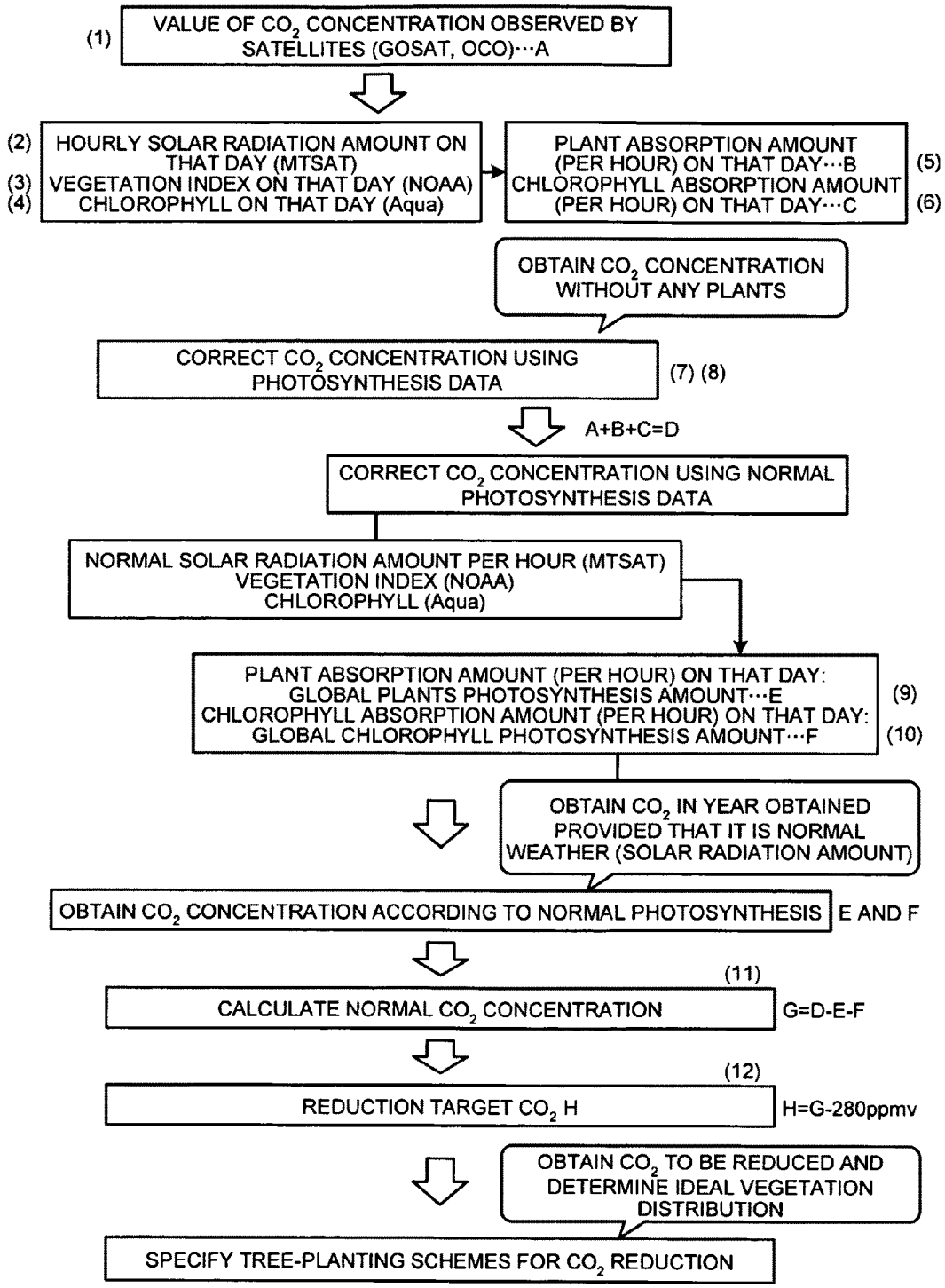
FIG. 2 is an explanatory view explaining an example of a process procedure of the $CO_2$ concentration correcting apparatus.

The overview and features of the $CO_2$ concentration correcting apparatus according to the first embodiment will be explained below with reference to FIGS. 1 and 2. FIG. 1 is a diagram for explaining the overview and features of the $CO_2$ concentration correcting apparatus according to the first embodiment. FIG. 2 is a diagram explaining the overview of processes performed by the $CO_2$ concentration correcting apparatus.

As illustrated in FIG. 1, the overview of the $CO_2$ concentration correcting apparatus represented in the first embodiment is that data on the $CO_2$ concentration, which is observed by the GOSAT and OCO, is corrected by considering vegetation data, the distribution of the amount of photosynthesis by chlorophyll, and changes in the amount of solar radiation on the basis of $CO_2$ concentration data, the amount of solar radiation, vegetation data (vegetation index SR), which is the distribution of plants, and the chlorophyll concentration that are obtained by a plurality of observation satellites (GOSAT, OCO, MTSAT, NOAA satellite, and Aqua) through their observations.

Specifically, the observation satellites obtain a high-resolution solar radiation value, a vegetation index, and a chlorophyll distribution over a wide range, and yearly deviations of the $CO_2$ concentration are corrected (evaluation by combining physical quantities that are acquired from the observation satellites is performed) to obtain a $CO_2$ concentration distribution without the effects from yearly climate changes. As described above, the amount of $CO_2$ that is absorbed by plant photosynthesis and chlorophyll photosynthesis according to changes in the amount of solar radiation due to yearly variations in weather is not considered for the conventional data on $CO_2$ concentration on the earth. The main features of the first embodiment are that the $CO_2$ concentration is corrected in a manner that the $CO_2$ concentration, which is observed by the GOSAT, is acquired and variations in the amount of $CO_2$, which is absorbed by the activities of vegetation, and variations in the amount of $CO_2$, which is absorbed by the activities of chlorophyll according to changes in the amount of solar radiation, with changes in the amount of solar radiation are calculated.

Planting plants, which photosynthesize actively, in regions where the $CO_2$ concentration is high and the amount of solar radiation is large and supplying the sea with iron where the chlorophyll concentration is high are effective methods to reduce excessive $CO_2$ on the earth. To do so, it is necessary to acquire accurate values of the $CO_2$ concentration, and it is desirable that changes in the amount of solar radiation that differ yearly have no effect on the observed values.

Because the $CO_2$ concentration is increasing year by year, even if measured values from the GOSAT in the past three years are averaged, data that can be dealt with as a normal cannot be obtained. However, in the first embodiment, a $CO_2$ concentration value according to a normal solar radiation amount (climate value) can be calculated by calculating the $CO_2$ concentration (total $CO_2$ data D) obtained provided that no plants exist and by then incorporating the amount of photosynthesis that is calculated on the basis an amount of solar radiation, which is a normal (for example, a mean of the amount of solar radiation in the past three years), into the calculated $CO_2$ concentration.

A correcting process of the $CO_2$ concentration correcting apparatus according to the first embodiment will be explained below with reference to FIGS. 1 and 2. Specifically, first, as illustrated in FIGS. 1 and 2, observation data on the $CO_2$ concentration that is measured by the GOSAT and data on the $CO_2$ concentration distribution on the earth, which is estimated by the OCO, are acquired and the data is stored as $CO_2$ concentration data A (see (1) in FIGS. 1 and 2).

MTSAT observes the amount of solar radiation per hour (hourly) in a day. Solar radiation amount data is acquired from image data that represents the amount of solar radiation, which is observed by MTSAT, and the solar radiation amount data is stored (see (2) in FIGS. 1 and 2). The solar radiation amount data that is obtained by MTSAT through observations is image data that is obtained per hour in each predetermined region on the earth (each predetermined lattice).

The NOAA satellite obtains vegetation data on plants on the earth through observations. The vegetation data (vegetation index SR) is acquired, and the vegetation index SR is stored (see (3) in FIGS. 1 and 2). The vegetation data (the vegetation index SR) that is obtained by the NOAA satellite through observations is image data of a monthly mean that is acquired from each predetermined region on the earth (each predetermined lattice).

Aqua observes the amount of chlorophyll in the ocean. The observed amount of chlorophyll is acquired and stored (see (4) in FIGS. 1 and 2). Aqua observes the amount of chlorophyll twice a day. Data on chlorophyll that is observed by Aqua is image data of a monthly mean that is acquired from each predetermined region on the earth (each predetermined lattice).

The amount of $CO_2$ (NEP value) absorbed by photosynthesis according to the vegetation distribution of plants is calculated on the basis of the vegetation data (vegetation index SR), which is obtained by the NOAA satellite through observations, and hourly solar radiation amount data. The calculated NEP value is stored as a plant absorption amount B (see (5) in FIGS. 1 and 2). In other words, the NEP value concerning plants is a net ecosystem production (the amount of absorption of $CO_2$ concentration) based on the vegetation data, which is obtained from the hourly solar radiation amount data. Specifically, the NEP value concerning plants is a numerical value that represents how much $CO_2$ (gC) is absorbed in a predetermined region in a region of 1 $m^2$) per month. For example, it is observed that, while the NEP value that is observed in forests in Hokkaido is close to 0 from October to April where the temperature is relatively low, it increases to 230 ($gC/m^2$/month) in June.

The amount of absorbed $CO_2$ (NEP value) according to changes (transition) in chlorophyll living in the ocean is calculated on the basis of the amount of chlorophyll, which is obtained by Aqua through observations, and the hourly solar radiation amount data. The calculated NEP value is stored as a chlorophyll absorption amount C (see (6) in FIGS. 1 and 2). In other words, the NEP value concerning chlorophyll is the amount of absorption of $CO_2$ concentration according to the chlorophyll concentration distribution, which is obtained from data on the amount of solar radiation, which is the normal.

Furthermore, the monthly mean of hourly solar radiation amount at least in the past three years is calculated as a cumulative average solar radiation amount. The data on the calculated amount of solar radiation is stored as cumulative average solar radiation amount data (see (7) in FIGS. 1 and 2).

Total $CO_2$ data D is calculated from the $CO_2$ concentration on the earth (the $CO_2$ concentration data A) that is obtained by the GOSAT through observations, the plant absorption amount B due to photosynthesis according to the vegetation distribution of plants, which is an amount calculated on the basis of the vegetation data (the vegetation index SR) and the hourly solar radiation amount data, and the chlorophyll absorption amount C due to photosynthesis according to changes (transition) in the amount of chlorophyll, which is data calculated on the basis of the amount of chlorophyll and the hourly solar radiation amount data (see (8) in FIGS. 1 and 2). Specifically, the total $CO_2$ data D is obtained by adding up the $CO_2$ concentration data A, the plant absorption amount B, and the chlorophyll absorption amount C (A+B+C=D). By performing these processes with respect to the past one month, a state is assumed where plants and chlorophyll all disappeared one month before, and the $CO_2$ concentration in such a state is calculated.

In addition, photosynthesis amount distribution data is generated on the basis of the data on vegetation on the earth (the vegetation index SR) and the cumulative average solar radiation amount (the hourly mean solar radiation amount data), which is the hourly mean of the amount of solar radiation in a month. The generated photosynthesis amount distribution data is stored as global plant photosynthesis amount E concerning plants (see (9) in FIGS. 1 and 2). The global plant photosynthesis amount E concerning plants is data that is accumulated hourly in each predetermined region on the earth (each predetermined lattice) for a month.

Photosynthesis amount distribution data is generated on the basis of the amount of chlorophyll living in the ocean and the cumulative average solar radiation amount (hourly mean solar radiation amount data), which is the hourly mean of the amount of solar radiation in a month. The generated photosynthesis amount distribution data is stored as a global chlorophyll photosynthesis amount F concerning chlorophyll (see (10) in FIGS. 1 and 2). Like the global plant photosynthesis amount E, the global chlorophyll photosynthesis amount F is data that is accumulated hourly in each predetermined region on the earth (each predetermined lattice) for a month.

Difference data obtained by subtracting the global plant photosynthesis amount E and the global chlorophyll photosynthesis amount F from the total $CO_2$ data D is calculated as $CO_2$ concentration G, which is a normal (D−E−F=G) (see (11) in FIGS. 1 and 2). In other words, the $CO_2$ concentration G, which is the normal, is calculated as the net $CO_2$ concentration on the earth. The $CO_2$ concentration, which is the normal, contains the value (280 ppmv) that can exist in nature. Therefore, by subtracting 280 ppmv from the $CO_2$ concentration amount G, which is the normal, a value is obtained as a reduction target $CO_2$ amount H. The reduction target $CO_2$ amount H serves as the amount of $CO_2$ that serves as a target for reduction by additional tree planting.

Accordingly, the $CO_2$ concentration to be reduced is obtained and the ideal vegetation distribution can be determined. Thus, vegetation schemes for $CO_2$ reduction can be embodied. In other words, an area where the reduction target $CO_2$ amount H is large is an area to which green campaigns are carried out using plants (tree planting) or an area where ocean environmental improvement is made. Green campaigns for tree-planting or ocean environment improvement to cancel the difference will be performed. Specifically, plants may be planted in regions where the amount of $CO_2$ is large. In the ocean, to increase the amount of chlorophyll that absorbs $CO_2$ by photosynthesis, iron particles may be dispersed over the sea surface by, for example, an aircraft after sufficient environmental assessment has been performed.

From the reduction target $CO_2$ amount H, prospective plants and trees that should be planted on the earth and the size and number of these plants and trees (per unit area) can be calculated by estimation in consideration of the seasons and regions.

Configuration of $CO_2$ Concentration Correcting Apparatus 1

Figure 3:
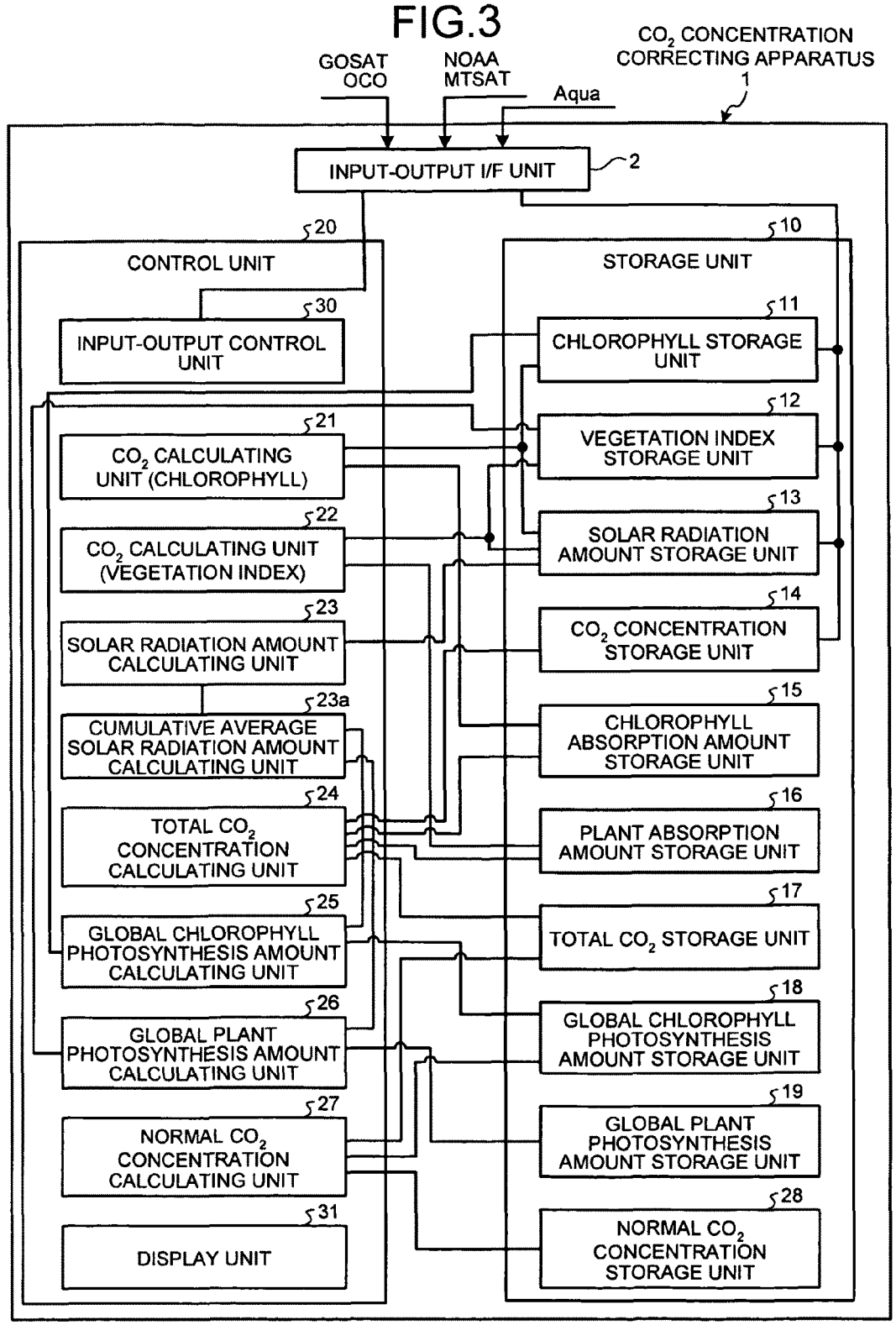
FIG. 3 is a block diagram of a configuration of the $CO_2$ concentration correcting apparatus.

The configuration of the $CO_2$ concentration correcting apparatus 1 will be explained below with reference to FIG. 3. FIG. 3 is a block diagram of the configuration of the $CO_2$ concentration correcting apparatus according to the first embodiment. As illustrated in FIG. 3, the $CO_2$ concentration correcting apparatus 1 includes an input-output I/F unit 2, a storage unit 10, a control unit 20, and an input-output control unit 30.

The input-output I/F unit 2 controls input and output of observation data obtained by the GOSAT, OCO, MTSAT, NOAA satellite, and Aqua through observations. The input-output control unit 30 controls data transfer between the input-output I/F unit 2 and the storage unit 10 and between the input-output I/F unit 2 and the control unit 20.

The storage unit 10 stores various types of data that is obtained by a plurality of satellites (GOSAT, OCO, MTSAT, NOAA satellite, and Aqua) through observations and data and programs necessary for various processes performed by the control unit 20. The storage unit 10 includes, particularly as those closely related to the present invention, a chlorophyll storage unit 11, a vegetation index storage unit 12, a solar radiation amount storage unit 13, a $CO_2$ concentration storage unit 14, a chlorophyll absorption amount storage unit 15, a plant absorption amount storage unit 16, a total $CO_2$ storage unit 17, a global chlorophyll photosynthesis amount storage unit 18, and a global plant photosynthesis amount storage unit 19.

The control unit 20 includes an internal memory for storing control programs, such as an operation system (OS), programs that define various process procedures, and necessary data. The control unit 20 includes, particularly as those closely related to the present invention, a $CO_2$ calculating unit 21 (chlorophyll), a $CO_2$ calculating unit 22 (vegetation index), a solar radiation amount calculating unit 23, a cumulative average solar radiation amount calculating unit 23a, a total $CO_2$ concentration calculating unit 24, a global chlorophyll photosynthesis amount calculating unit 25, an global plant photosynthesis amount calculating unit 26, a normal $CO_2$ concentration calculating unit 27, and a display unit 31.

The chlorophyll storage unit 11 acquires data on the amount of chlorophyll on the earth, which is observed by Aqua. The chlorophyll amount data is stored with respect to each predetermined region on the earth (each predetermined lattice).

The vegetation index storage unit 12 acquires the data on vegetation on the earth, which is observed by the NOAA satellite, (vegetation index SR) and stores the vegetation data. The vegetation data is stored with respect to each predetermined region on the earth (each predetermined lattice).

Figure 4:
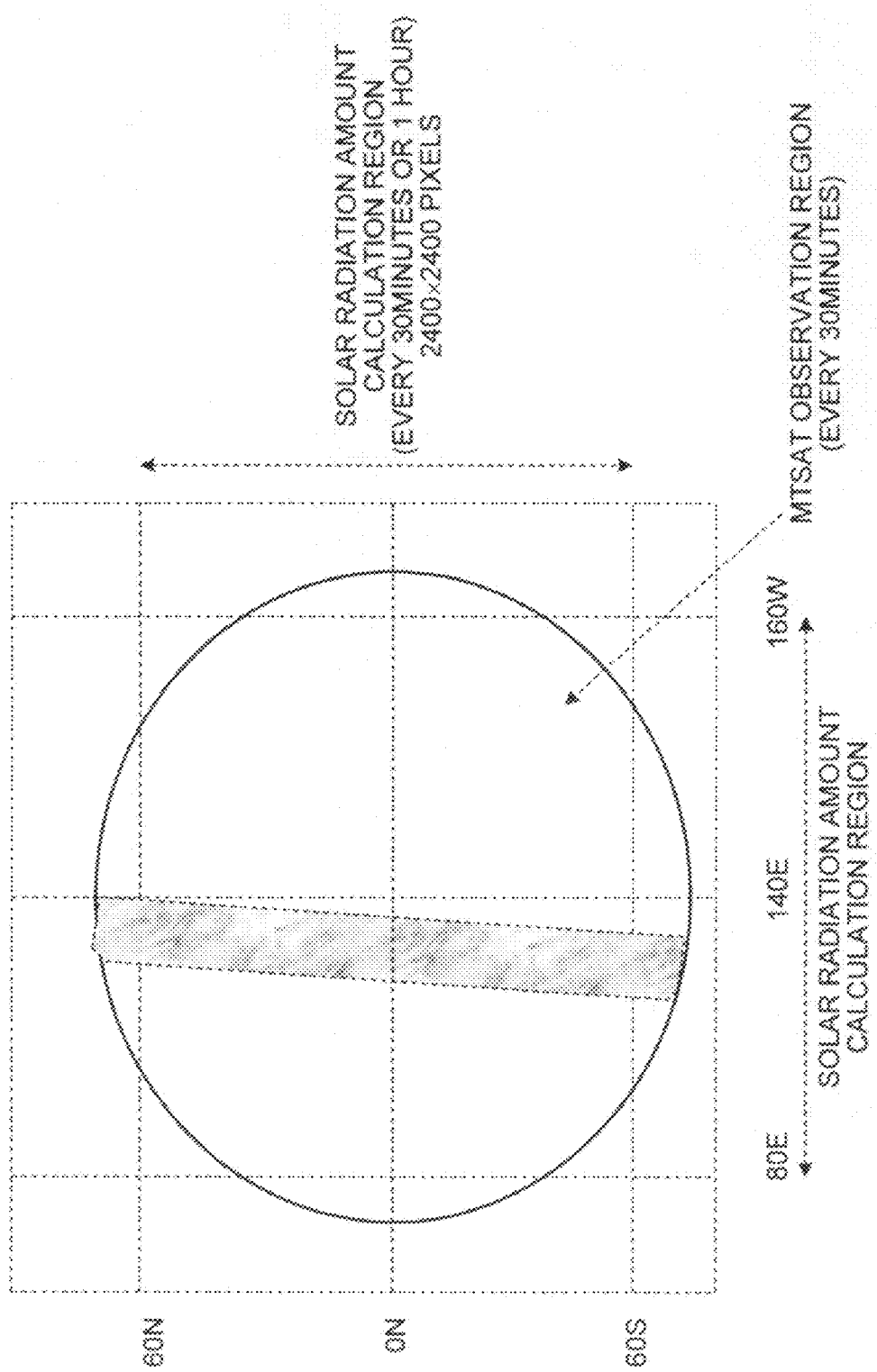
FIG. 4 is a diagram explaining an observation region of the GOSAT and MTSAT and a region of calculation of the amount of solar radiation.

The solar radiation amount storage unit 13 acquires the data on the amount of solar radiation on the earth, which is observed by MTSAT, and stores the data. The solar radiation amount data is stored per hour with respect to each predetermined region on the earth (each predetermined lattice). FIG. 4 is a diagram explaining the observation region of the GOSAT and MTSAT and the region of calculation of the amount of solar radiation. As illustrated in FIG. 4, the region surrounded by the large circle represents the observation region of MTSAT and represents an observation that is performed every 30 minutes. In addition, the shaded range represents the observation region of the GOSAT over a certain observation time period. The same point is observed once every three days. The GOSAT orbits the earth 14 times a day and observes the shaded range at 13:16 Japan local time.

In other words, as illustrated in FIG. 4, the data on the amount of solar radiation, which is observed by MTSAT, is image data that is acquired hourly in the region of 0.0125 of a lattice located between 60-degrees north latitude and 60-degrees south latitude (2400×2400 pixels). As illustrated in FIG. 4, the image data on the amount of solar radiation is data acquired at a time that is the same as the local time (13:16) of the observation by the GOSAT.

The $CO_2$ concentration storage unit 14 stores data on the $CO_2$ concentration that is observed by the GOSAT and OCO. The $CO_2$ concentration that is stored in the $CO_2$ concentration storage unit 14 is data that consists of a lattice resolution of about 80 km, which is obtained by the GOSAT through observations at the same point once every three days (see FIG. 4).

The chlorophyll absorption amount storage unit 15 stores the amount of $CO_2$ (NEP value) concerning chlorophyll, which is $CO_2$ absorbed according to changes (transition) in chlorophyll, which is an amount calculated by the $CO_2$ calculating unit 21 on the basis of the amount of chlorophyll stored in the chlorophyll storage unit 11 and the solar radiation amount data (hourly solar radiation amount) stored in the solar radiation amount storage unit 13.

The plant absorption amount storage unit 16 stores the amount of $CO_2$ (NEP value) concerning plants, which is $CO_2$ absorbed according to changes (transition) in the plant distribution, which is an amount calculated by the $CO_2$ calculating unit 22 on the basis of the vegetation index stored in the vegetation index storage unit 12 and the solar radiation amount data (hourly solar radiation amount) stored in the solar radiation amount storage unit 13.

The total $CO_2$ storage unit 17 stores data calculated by the total $CO_2$ concentration calculating unit 24 on the basis of the $CO_2$ concentration data, which is stored in the $CO_2$ concentration storage unit 14, the $CO_2$ absorption amount that changes according to the transition in the plant distribution, which is an amount stored in the plant absorption amount storage unit 16, and the chlorophyll-related $CO_2$ absorption amount that changes according to the transition in the existence of chlorophyll, which is an amount stored in the chlorophyll absorption amount storage unit 15. Specifically, the stored data is a value obtained by adding up the $CO_2$ concentration data, the $CO_2$ absorption amount based on the plant data, and the amount of $CO_2$ absorbed by chlorophyll.

The global chlorophyll photosynthesis amount storage unit 18 stores data that is calculated by the global chlorophyll photosynthesis amount calculating unit 25 on the basis of the amount of chlorophyll, which is stored in the chlorophyll storage unit 11, and the amount of solar radiation, which is calculated by the cumulative average solar radiation amount calculating unit 23a.

The global plant photosynthesis amount storage unit 19 stores data that is calculated by the global plant photosynthesis amount calculating unit 26 on the basis of the vegetation index, which is stored in the vegetation index storage unit 12, and the amount of solar radiation, which is calculated by the cumulative average solar radiation amount calculating unit 23a.

The $CO_2$ calculating unit 21 calculates the amount of $CO_2$ (NEP value) that is absorbed according to changes (transition) in chlorophyll on the basis of the amount of chlorophyll, which is stored in the chlorophyll storage unit 11, and the hourly solar radiation amount data, which is stored in the solar radiation amount storage unit 13.

Specifically, an ocean $CO_2$ partial pressure is calculated taking the ocean temperature of the ocean surface on the earth and the climate value of the surface salinity into consideration for the chlorophyll concentration, and thus the amount of $CO_2$ absorbed (NEP value of chlorophyll) according to changes in chlorophyll is calculated. Note that although the formula is omitted, the NEP value of chlorophyll can be calculated by multiplying the $CO_2$ partial pressure by the normal ratio of the hourly solar radiation amount data. The NEP value that is calculated by the $CO_2$ calculating unit 21 is stored in the chlorophyll absorption amount storage unit 15.

The $CO_2$ calculating unit 22 calculates the $CO_2$ concentration according to plants. Specifically, the amount of $CO_2$ (NEP value) absorbed according to changes (transition) in plants is calculated on the basis of the plant data, which is stored in the vegetation index storage unit 12, and the hourly solar radiation amount data, which is stored in the solar radiation amount storage unit 13. The $CO_2$ calculating unit 22 calculates the amount of $CO_2$ (NEP value) absorbed by photosynthesis according to the vegetation distribution of plants on the basis of the vegetation index SR, which is obtained by the NOAA satellite through observations, and the hourly solar radiation amount data, which is stored in the solar radiation amount storage unit 13.

In other words, observation for vegetation data (the vegetation index SR) by the NOAA satellite is performed twice a day. The vegetation data that is observed by the NOAA satellite is image data that is obtained in the region of each predetermined lattice. The vegetation index SR can be obtained on the basis of a reflectance (NIR) of an infrared sensor, which is mounted on the NOAA satellite, and a reflectance (VIS) of visible light (vegetation index SR=NIR/VIS).

The NEP value, which is used for the amount of absorbed $CO_2$ (balance) based on the vegetation index SR can be obtained as an approximate value using the vegetation index SR (simple ratio), the solar radiation normal ratio, and the constant a from the following Equation 1 where the solar radiation normal ratio is the ratio of the momentary value to the normal of the amount of solar radiation (average in one hour) and a is 25. The NEP value, which is calculated by the $CO_2$ calculating unit 22, is stored in the plant absorbance amount storage unit 16.

$$NEP = a(SR-1) \times \text{solar radiation normal ratio} \quad \text{(Equation 1)}$$

The solar radiation amount calculating unit 23 acquires the amount of solar radiation, which is observed by MTSAT, to calculate hourly solar radiation amount data. The solar radiation amount data, which is calculated by the solar radiation amount calculating unit 23, is stored in the solar radiation amount storage unit 13.

The cumulative average solar radiation amount calculating unit 23a calculates, as the cumulative average solar radiation amount, the hourly mean of the amount of solar radiation in a month in the past three years. The solar radiation amount data, which is calculated by the cumulative average solar radiation amount calculating unit 23a, is stored in the solar radiation amount storage unit 13.

The total $CO_2$ concentration calculating unit 24 adds up the $CO_2$ concentration data, which is stored in the $CO_2$ concentration storage unit 14, the $CO_2$ absorption amount that changes according to transition in the distribution of plants and that is stored in the plant absorption amount storage unit 16, and the $CO_2$ absorption amount that changes according to transition in the existence of chlorophyll and that is stored in the chlorophyll absorption amount storage unit 15. The total $CO_2$ concentration, which is calculated by the total $CO_2$ concentration calculating unit 24, is stored in the total $CO_2$ storage unit 17.

The amount of absorbed $CO_2$ that changes according to the amount of solar radiation and the transition in the distribution of plants and the transition in the existence of chlorophyll are explained with reference to FIG. 5.

Figure 5:
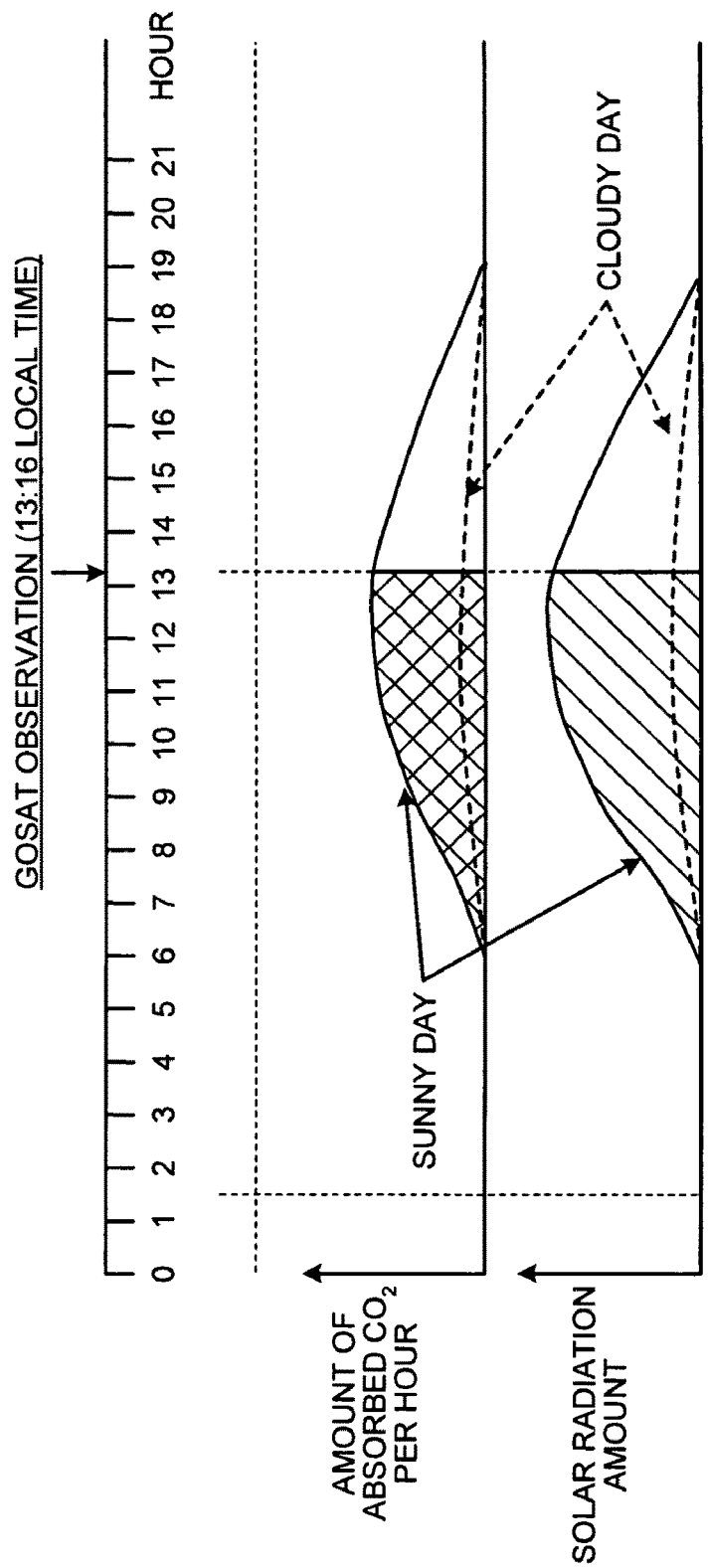
FIG. 5 is a diagram explaining the relation between the time of observation by the GOSAT in predetermined lattice coordinates, the amount of solar radiation at the coordinates, and the amount of $CO_2$ absorbed by plants and chlorophyll.

FIG. 5 is a diagram explaining the relation between the time of observation by the GOSAT at predetermined lattice coordinates, the amount of solar radiation at the coordinates, and the amount of $CO_2$ absorbed by plants and chlorophyll. The solid line in FIG. 5 represents a sunny day and a dashed line in FIG. 5 represents a cloudy day. As illustrated in FIG. 5, the amount of $CO_2$ absorbed by plants and chlorophyll increases on a sunny day compared to a cloudy day and the amount of absorbed $CO_2$ increases around noon (12:00-13:00 hrs). As illustrated in FIG. 5, the amount of absorbed $CO_2$ (NEP value) corresponding to the amount of solar radiation in the shaded portion is calculated, and correcting by adding the NEP value to the data on the $CO_2$ concentration observed by the GOSAT is performed. Note that the amount of $CO_2$ absorbed by plants and chlorophyll is a value obtained by accumulation from a month before.

The global chlorophyll photosynthesis amount calculating unit 25 calculates the global chlorophyll photosynthesis amount on the basis of the amount of chlorophyll, which is stored in the chlorophyll storage unit 11, and the amount of solar radiation, which is calculated by the cumulative average solar radiation amount calculating unit 23a. Specifically, the global chlorophyll photosynthesis amount, which is calculated by the global chlorophyll photosynthesis amount calculating unit 25, is calculated as chlorophyll-related photosynthesis amount distribution data from the solar radiation amount data (a mean in a month) obtained by averaging the amounts for a predetermined number of past years (at least three past years) and the latest vegetation data (a mean in a month). The chlorophyll-related photosynthesis amount distribution data, which is calculated by the global chlorophyll photosynthesis amount calculating unit 25, is stored in the global chlorophyll photosynthesis amount storage unit 18.

The global plant photosynthesis amount calculating unit 26 calculates the global plant photosynthesis amount from the vegetation data, which is stored in the vegetation index storage unit 12, and the amount of solar radiation (the vegetation index SR), which is calculated by the cumulative average solar radiation amount calculating unit 23a. Specifically, the global plant photosynthesis amount, which is calculated by the global plant photosynthesis amount calculating unit 26, is calculated as plant-related photosynthesis amount distribution data from the solar radiation amount data (a mean in a month) obtained by averaging the amounts for a predetermined number of past years (three past years) and the latest chlorophyll concentration. The photosynthesis distribution data on plants, which is calculated by the global plant photosynthesis amount calculating unit 26, is stored in the global plant photosynthesis amount storage unit 19.

Figure 6:
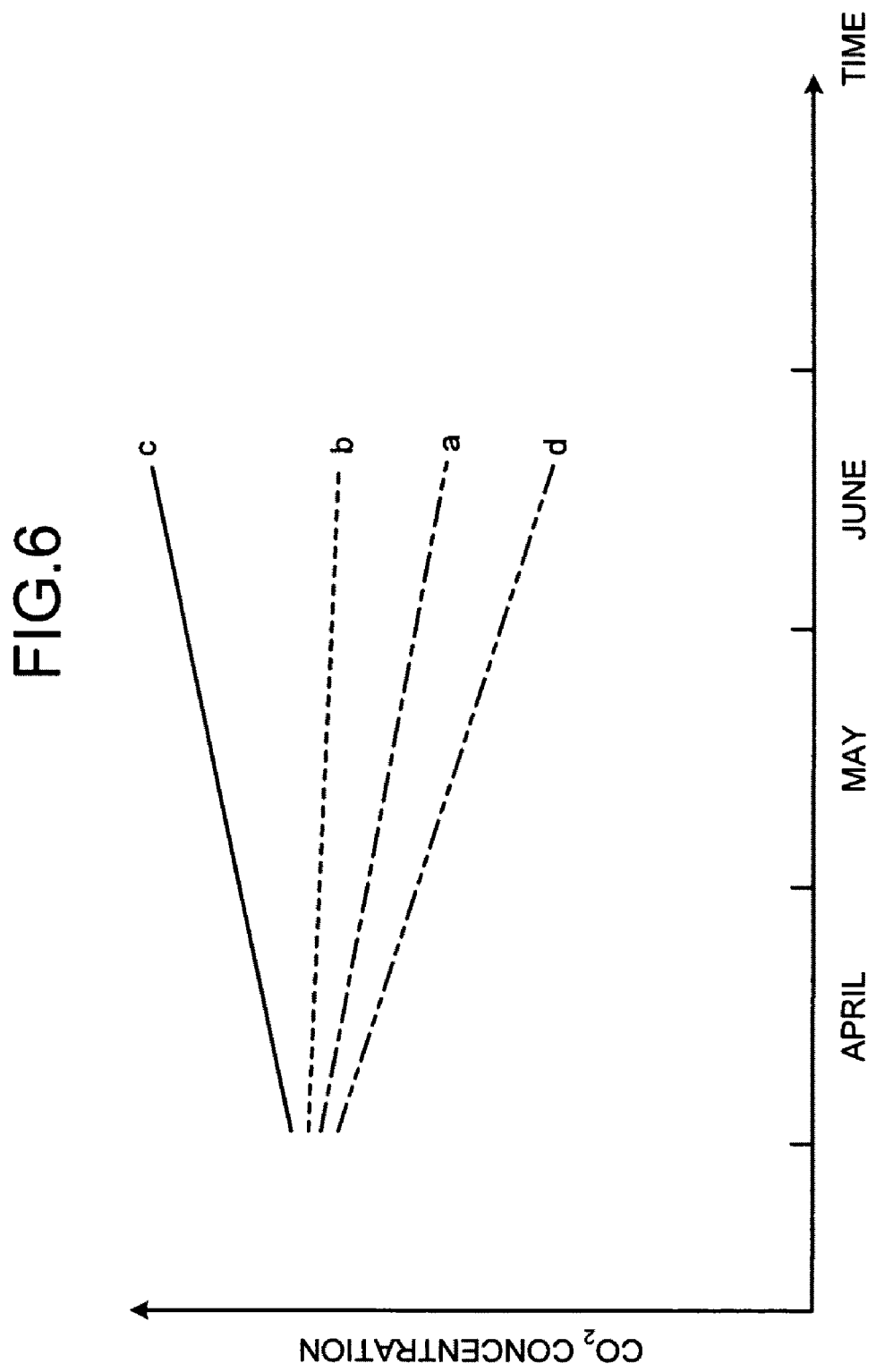
FIG. 6 is a diagram explaining transition of the $CO_2$ concentration with progress in time.

FIG. 6 is an explanatory diagram representing the transition of $CO_2$ over time variations. Specifically, the line chart a in FIG. 6 represents the yearly transition of $CO_2$ in a year where the amount of solar radiation from April to June, which is observed by the GOSAT, is larger than that in a normal year. As illustrated in FIG. 6, the amount of solar radiation increases from April to June and the $CO_2$ concentration decreases chronologically because of photosynthesis by plants and chlorophyll.

The line chart b represents the yearly transition of $CO_2$ that is obtained by correcting the line chart a using the normal solar radiation amount. As illustrated in FIG. 6, the $CO_2$ concentration slightly increases, compared to the $CO_2$ concentration in the line chart a, such that that $CO_2$ concentration accords not with the amount of solar radiation in the year with a large amount of solar radiation but to the normal solar radiation amount. The line chart c represents the yearly transition of $CO_2$ in the case where no plant and no chlorophyll exist on the earth. As illustrated in the line chart c, the $CO_2$ concentration increases as time progresses. The line chart d represents the transition in the $CO_2$ concentration that is corrected using the normal solar radiation amount in a year where the amount of solar radiation from April to June is smaller than that in a normal year.

The normal $CO_2$ concentration calculating unit 27 calculates the $CO_2$ concentration from the total $CO_2$ concentration, which is stored in the total $CO_2$ storage unit 17, the amount of chlorophyll, which is stored in the global chlorophyll photosynthesis amount storage unit 18, and the vegetation index, which is stored in the global plant photosynthesis amount storage unit 19, and stored as a normal $CO_2$ concentration storage unit 28.

The display unit 31 includes a display or a monitor that displays various types of information. For example, the display unit 31 displays observation data, which is obtained by each satellite, such as the GOSAT, MTSAT, NOAA satellite, and Aqua, through their observations with respect to each predetermined region on the earth (each predetermined lattice). The effects from the distribution of plants and of chlorophyll can be visually confirmed using the image data that is displayed on the display unit 31. In addition, effects from green campaigns can be visually confirmed.

Overall Process Procedure of $CO_2$ Concentration Correcting Apparatus 1

Figure 7:
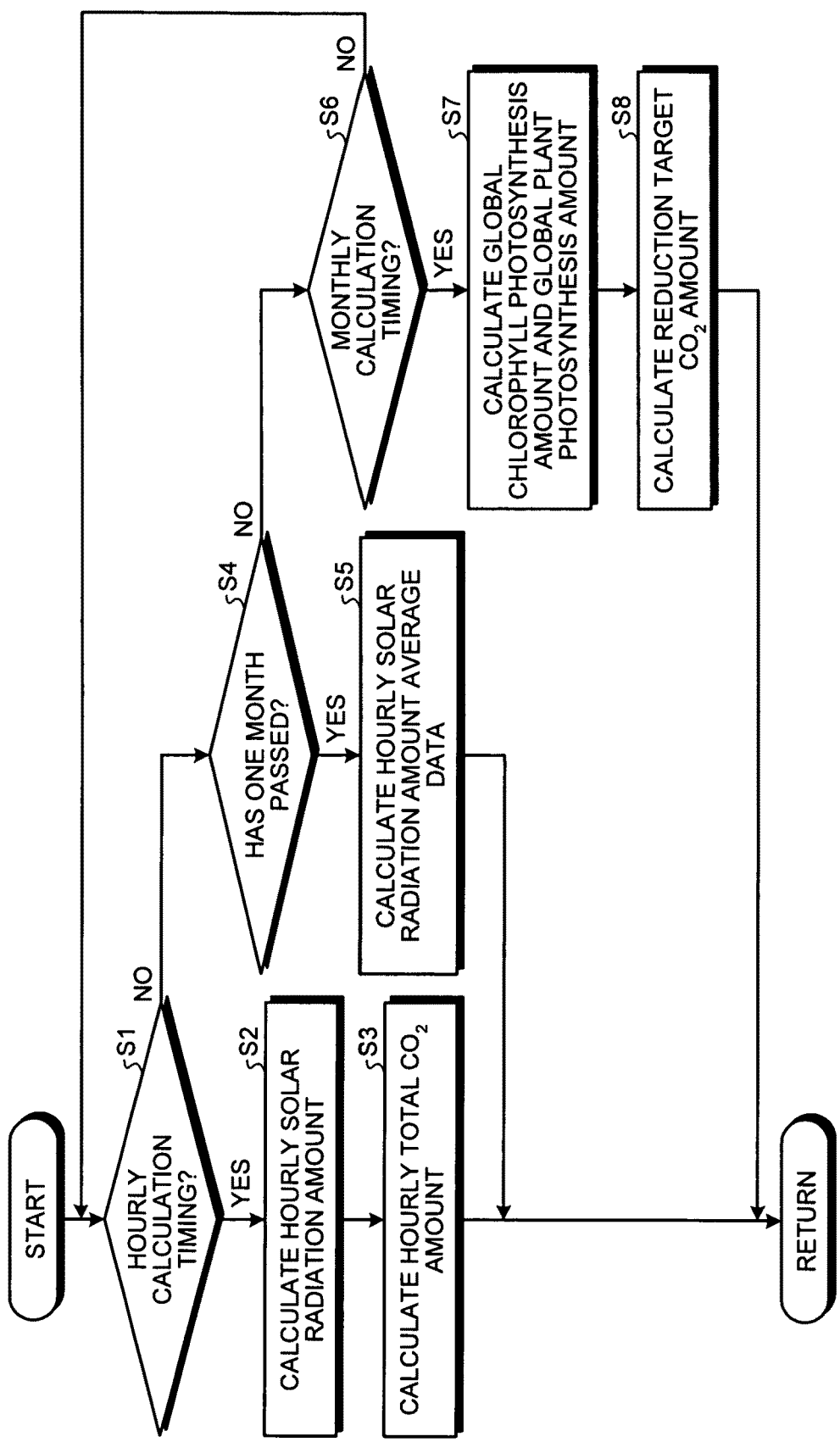
FIG. 7 is a flowchart explaining the process procedure of the $CO_2$ concentration correcting apparatus.

FIG. 7 is a flowchart of an overall process procedure of the $CO_2$ concentration correcting apparatus 1. Specifically, as the flowchart in FIG. 7 illustrates, it is determined whether it is hourly calculation timing (per hour) of observation data from the observation satellites (step S1). When it is determined that it is hourly calculation timing (per hour) of the observation data from the observation satellites (YES at step S1), data obtained by each of the observation satellites (GOSAT, MTSAT, NOAA satellite, Aqua) through observation is acquired and a monthly mean chlorophyll amount and a vegetation index of plants, and an hourly solar radiation amount are calculated (step S2). Specifically, the chlorophyll amount, the plant data, and the solar radiation amount are observed respectively by Aqua, the NOAA satellite, and MTSAT and calculated. Subsequently, the hourly total $CO_2$ concentration is calculated (step S3).

In contrast, when it is determined that it is not hourly calculation timing by determination at step S1 (NO at step S1), it is then determined whether one month has passed since a predetermined time (step S4). When one month has passed since the predetermined time (YES at step S4), hourly solar radiation amount average data is calculated (step S5), and the process goes back to step S1.

In contrast, when it is determined that one month has not passed since the predetermine time by determination at step S4, it is then determined whether it is monthly calculation timing (step S6). When it is determined that it is monthly calculation timing (YES at step S6) a monthly global chlorophyll photosynthesis amount F concerning chlorophyll and a global plant photosynthesis amount E concerning plants are calculated (step S7).

As described above, the global chlorophyll photosynthesis amount F is calculated on the basis of the amount of chlorophyll, which is stored in the chlorophyll storage unit 11, and the amount of solar radiation, which is calculated by the cumulative average solar radiation amount calculating unit 23*a*. The global plant photosynthesis amount E is calculated on the basis of the vegetation index SR, which is stored in the vegetation index storage unit 12, and the amount of solar radiation, which is calculated by the cumulative average solar radiation amount calculating unit 23*a*.

Subsequently, the amount of photosynthesis (the amount of $CO_2$ to be reduced) that should be increased as green campaigns is calculated on the basis of the global chlorophyll photosynthesis amount information and the global plant photosynthesis amount information that are calculated at step S7 (step S8) and the process goes back to step S1. As described above, the $CO_2$ concentration G, which is the normal, is calculated by calculating difference data that is obtained by subtracting the global plant photosynthesis amount E and the global chlorophyll photosynthesis amount F from the total $CO_2$ data D.

As described above, the $CO_2$ concentration correcting apparatus 1 according to the present invention is configured to calculate an hourly $CO_2$ concentration, an amount of solar radiation, and plant-chlorophyll distribution information from predetermined satellites through observation, calculate the concentration of $CO_2$ absorbed by plants hourly, calculate a total $CO_2$ concentration by adding up the $CO_2$ concentration on the earth and the concentration of $CO_2$ that is absorbed by plant-chlorophyll, calculate, as a mean, a concentration of $CO_2$ that is absorbed according to changes in the distribution of the plant-chlorophyll on the basis of a monthly mean solar radiation amount and the plant-chlorophyll distribution information, and perform correction for calculating a normal $CO_2$ concentration by subtracting the mean $CO_2$ concentration from the total $CO_2$ concentration. This corrects bias errors of the $CO_2$ concentration due to yearly variations in the weather. Accordingly, a $CO_2$ concentration with small errors resulting from the yearly weather variations can be estimated, which results in effective green campaigns.

The distribution of $CO_2$ varies time to time because of the circulation of atmosphere. Provided that the source is almost the same, it can be assumed that the distribution of $CO_2$ is uniform in a time scale of about one month. Accordingly, monthly mean hourly distribution data can be generated to obtain spatio-temporally uniform data. The monthly mean shifted day by day may be generated every day to incorporate the latest data. It is desirable to use observation data that is not patio-temporally averaged for the $CO_2$ concentration that incorporates the NEP value, which is estimated from the hourly solar radiation amount data.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. An apparatus comprising:
    an observed $CO_2$ amount storage unit that stores an observed $CO_2$ amount that is an amount of $CO_2$ that is observed in an observation region;
    a plant-chlorophyll distribution information storage unit that stores plant-chlorophyll distribution information on distribution of plant-chlorophyll in the observation region;
    a solar radiation amount storage unit that stores an amount of solar radiation in the observation region;
    an absorbed $CO_2$ amount calculating unit that calculates an absorbed $CO_2$ amount that is an amount of $CO_2$ that is absorbed by the plant-chlorophyll on the basis of the plant-chlorophyll distribution information and the amount of solar radiation;
    a total $CO_2$ amount calculating unit that calculates a total $CO_2$ amount by adding up the observed $CO_2$ amount and the absorbed $CO_2$ amount;
    an average solar radiation amount storage unit that stores an average solar radiation amount in the observation region;

an average absorbed $CO_2$ amount calculating unit that calculates an average absorbed $CO_2$ amount that is an average amount of $CO_2$ that is absorbed by plant-chlorophyll when a solar radiation amount is the average solar radiation amount; and a corrected $CO_2$ amount calculating unit that calculates a corrected $CO_2$ amount by subtracting the average absorbed $CO_2$ amount from the total $CO_2$ amount.

2. The apparatus according to claim 1, wherein the plant-chlorophyll distribution information storage unit stores vegetation distribution information on plants on the ground or chlorophyll distribution information on chlorophyll in the ocean, or stores the vegetation distribution information and the chlorophyll distribution information.

3. The apparatus according to claim 1, wherein the average solar radiation amount is an amount that is obtained by averaging average solar radiation amounts in a predetermined period including the time at which the observed $CO_2$ amount is observed in past few years.

4. A method comprising:
storing an observed $CO_2$ amount that is an amount of $CO_2$ that is observed in an observation region;
storing plant-chlorophyll distribution information on distribution of plant-chlorophyll in the observation region;
storing an amount of solar radiation in the observation region;
calculating, using a processor, an absorbed $CO_2$ amount that is an amount of $CO_2$ that is absorbed by the plant-chlorophyll on the basis of the plant-chlorophyll distribution information and the amount of solar radiation;
calculating a total $CO_2$ amount by adding up the observed $CO_2$ amount and the absorbed $CO_2$ amount;
storing an average solar radiation amount in the observation region;
calculating, using the processor, an average absorbed $CO_2$ amount that is an average amount of $CO_2$ that is absorbed by plant-chlorophyll when a solar radiation amount is the average solar radiation amount; and
calculating, using the processor, a corrected $CO_2$ amount by subtracting the average absorbed $CO_2$ amount from the total $CO_2$ amount.

5. The method according to claim 4, wherein the storing the plant-chlorophyll distribution information includes storing vegetation distribution information on plants on the ground or chlorophyll distribution information on chlorophyll in the ocean, or stores the vegetation distribution information and the chlorophyll distribution information.

6. A non-transitory computer readable storage medium having stored therein a computer program causing a computer to execute a process comprising:
storing an observed $CO_2$ amount that is an amount of $CO_2$ that is observed in an observation region;
storing plant-chlorophyll distribution information on distribution of plant-chlorophyll in the observation region;
storing an amount of solar radiation in the observation region;
calculating an absorbed $CO_2$ amount that is an amount of $CO_2$ that is absorbed by the plant-chlorophyll on the basis of the plant-chlorophyll distribution information and the amount of solar radiation;
calculating a total $CO_2$ amount by adding up the observed $CO_2$ amount and the absorbed $CO_2$ amount;
storing an average solar radiation amount in the observation region;
calculating an average absorbed $CO_2$ amount that is an average amount of $CO_2$ that is absorbed by plant-chlorophyll when a solar radiation amount is the average solar radiation amount; and
calculating a corrected $CO_2$ amount by subtracting the average absorbed $CO_2$ amount from the total $CO_2$ amount.

* * * * *